United States Patent [19]
Richardson

[11] Patent Number: 5,788,695
[45] Date of Patent: Aug. 4, 1998

[54] PATIENT-OPERATED ORTHOPEDIC DEVICES

[76] Inventor: James Bruce Richardson, Westminster House, Old Chirk Road, Gobowen, Oswestry, Shropshire SY11 3LW, United Kingdom

[21] Appl. No.: 353,198

[22] Filed: Dec. 9, 1994

[30] Foreign Application Priority Data

Dec. 15, 1993 [GB] United Kingdom ............ 9325698

[51] Int. Cl.[6] ...................................... A61B 17/66
[52] U.S. Cl. ...................................... 606/57; 606/54
[58] Field of Search ........................ 606/54, 55, 56, 606/57, 58, 59, 86, 90

[56] References Cited

U.S. PATENT DOCUMENTS 5,108,393  4/1992  Ruffa .

FOREIGN PATENT DOCUMENTS

| A0 383 419 | 8/1990 | European Pat. Off. . |
|---|---|---|
| A0 420 430 | 4/1991 | European Pat. Off. . |
| A2 574 653 | 6/1986 | France . |
| A24 37 752 | 2/1976 | Germany . |
| A41 09 760 | 10/1991 | Germany . |
| U92 14 550 | 3/1994 | Germany . |
| A8 802 277 | 4/1990 | Netherlands . |
| 29174 | of 1913 | United Kingdom . |
| WOA88 02618 | 4/1988 | WIPO . |

*Primary Examiner*—Guy V. Tucker
*Attorney, Agent, or Firm*—Hopgood, Calimafde, Kalil & Judlowe

[57] ABSTRACT

The invention serves patients having a fractured bone wherein separate parts of the bone have been immobilized by an external axial fixator, and the invention provides patient-operated mechanical structure to enable him to transiently distract spaced bone-anchored regions of the fixator. In one embodiment, the patient-operated mechanism is in the form of an accessory that is detachably mounted to the fixator; in another embodiment, the patient-operated mechanism is embodied in an external axial fixator, preferably of the so-called dynamic variety.

33 Claims, 7 Drawing Sheets

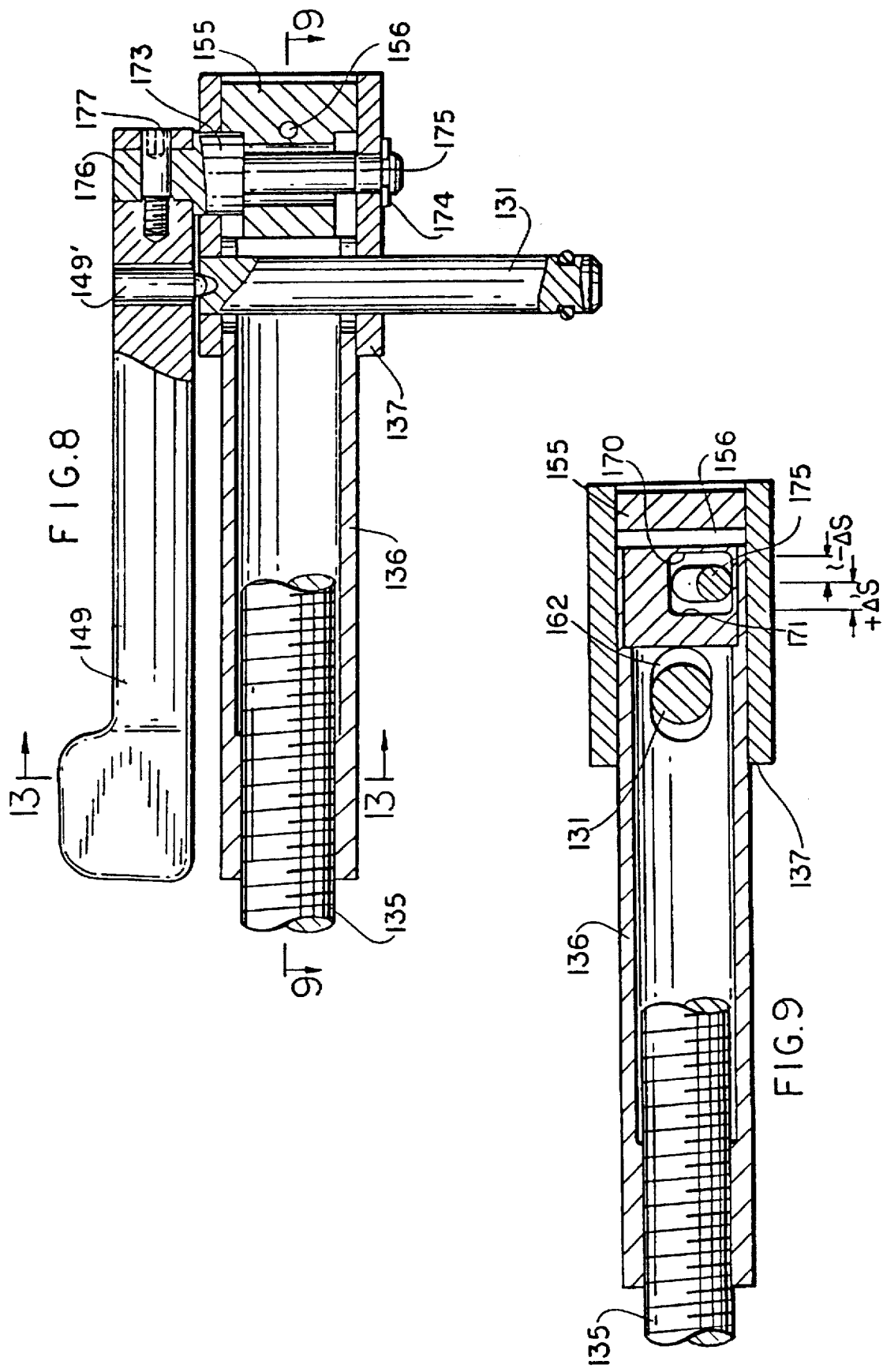

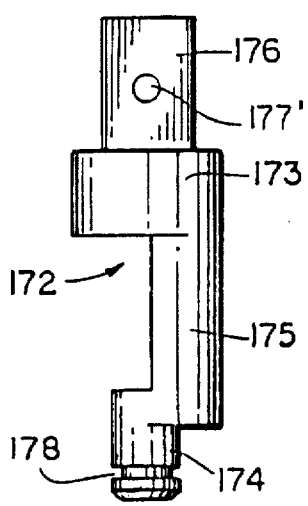
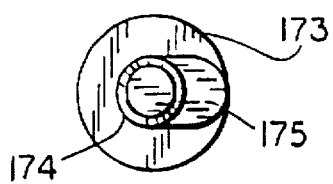
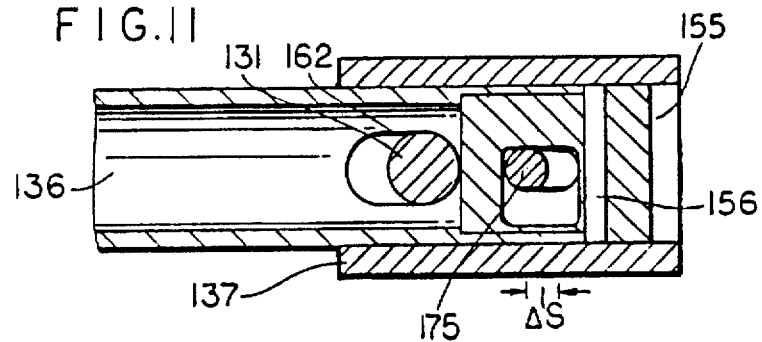
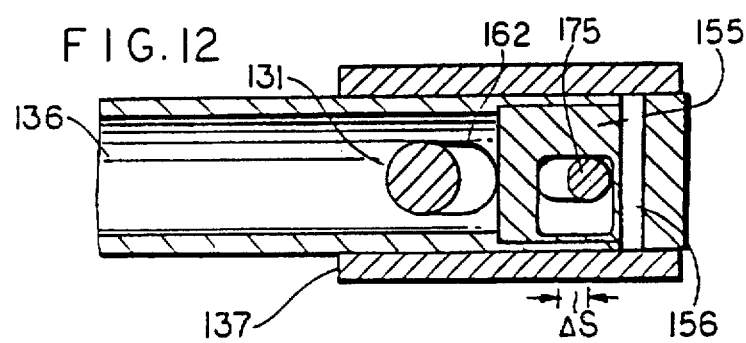
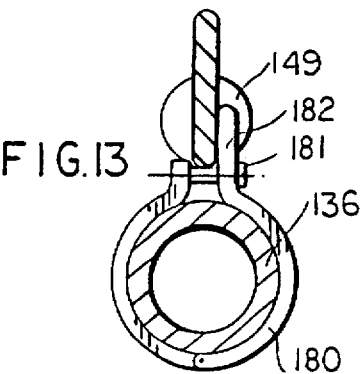
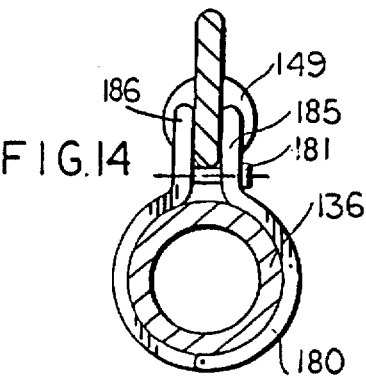

PATIENT-OPERATED ORTHOPEDIC DEVICES

BACKGROUND OF THE INVENTION

The invention relates to orthopedic devices in aid of bone-fracture repair and, in particular, to a patient-operated device for stimulated transient distraction of fractured components of a bone.

External fixators of the nature disclosed in U.S. Pat. No. Re. 31,809 and U.S. Pat. No. 4,621,627 rely upon an elongate central body of selectively adjustable length, with a bone-screw or bone-pin anchoring clamp at each longitudinal end of the body, with preferably a selectively locked ball-joint connection between each anchoring clamp and the body end to which it is connected. Selectively available body length involves telescoping body parts which are keyed against rotation and which can be secured to each other to hold a given setting of longitudinal span between the anchoring clamps. Provision is made for periodic precision increments of length to be made in the clamped relation of the telescoping body parts, by employing a length-adjusting jacking mechanism which may be an accessory device used by the surgeon to periodically adjust overall fixator-body length, in the course of a number of weeks of healing repair of the fracture; the accessory device is detachably applicable to the respective fixator-body parts, for incrementally jacking the fixator-body parts while momentarily releasing the secured relation of these body parts, the secured condition of the body parts being re-established before detaching the jacking mechanism.

In the course of normal leg fracture repair with such fixators, there is a period of several weeks during which the fixator-braced fracture is subjected to weight-bearing, i.e., the patient must stand and learn to walk with the clamped fixator. At the outset of this period, the fixator (via its bone-screw or bone-pin anchorages) takes almost all of the patient's body weight, and in the ensuing course of time the fidelity of bone-screw or bone-pin anchorage to the fractured bone gradually degrades, thus causing the healing bone to assume an increasing fraction of transient weight-bearing loads, as when walking. The nature of such transient loads is one of transient compressional loading of the fracture, which has been identified as a therapeutic aid that enhances the strength and the speed of bone repair, with shortened duration of the period of the patient's need for his fixator.

Recognition of the therapeutic value of periodic transient compression during the weight-bearing phase of bone-fracture repair has given rise to various modifications of external-fixator construction, so as to provide for more control of transient compressional loading. Such devices are sometimes called dynamic axial fixators, as in the case of U.S. Pat. No. 5,320,622. Other forms of such devices are disclosed in Sturtzkopf, et al. U.S. Pat. No. 5,026,372 and in Harris, et al. U.S. Pat. No. 4,502,473.

Applicant has discovered that therapy involving transient distraction of a fracture is accompanied by callus development at the fracture site, to an extent which exceeds and which is superior to that resulting from transient compression associated with or in replication of the weight-bearing phenomenon discussed above. Moreover, therapy involving transient distraction has no relation or analogy to weight-bearing, and applicant has found that transient distraction therapy does not require that the patient shall yet have progressed to the weight-bearing phase of fracture repair.

BRIEF STATEMENT OF THE INVENTION

It is an object of the invention to provide an improved device and method for accelerated repair of a fractured bone.

Another object is to meet the above object with a device which can be patient-operated without need for external power supply.

A specific object is to meet the above objects with an accessory device which is applicable to existing commercially available external fixators and which is also applicable to a patient who is already fitted with and using an external fixator.

Another specific object is to provide in an external fixator for patient-operated periodic distraction of the fracture.

A general object is to meet the above objects with accessory construction which is mechanically simple, readily patient-operated, and functionally reliable.

The invention in a preferred form achieves these objects by providing the patient with a simple hand-operated mechanical device for removable application to the respective longitudinal ends of a dynamic external axial fixator, such that a patient's hand-cranked actuation will induce a transient distraction of the bone-anchored ends of the fixator, and therefore transient distraction at the fracture site. In another embodiment, the patient-operated distraction feature is a built-in part of a dynamic external fixator.

DESCRIPTION OF THE DRAWINGS

Preferred and illustrative embodiments of the invention will be described in detail, in conjunction with the accompanying drawings, in which:

FIG. 3A is a fragmentary view similar to FIG. 3, but showing a modification of the right end of FIG. 3;

FIG. 8 is a view in side elevation, partly broken-away and in longitudinal section, for another embodiment;

FIG. 9 is a longitudinal section of the embodiment of FIG. 8, taken at 9—9 of FIG. 8;

FIG. 10A is a view in side elevation of a distraction-cam element of FIGS. 8 and 9;

FIG. 10B is an end view of the element of FIG. 10A;

FIG. 11 is a fragmentary view of distraction-actuating components of FIG. 8, for an actuated distraction condition;

FIG. 12 is a view similar to FIG. 11, for an actuated compression condition;

FIG. 13 is a simplified view of a first clamp structure applied to the device of FIGS. 8 and 9, to determine one phase of use, the section being taken at 13—13 in FIG. 8; and FIG. 14 is a view similar to FIG. 13, to determine another phase of use.

DETAILED DESCRIPTION OF THE INVENTION

Figures 1, 2:
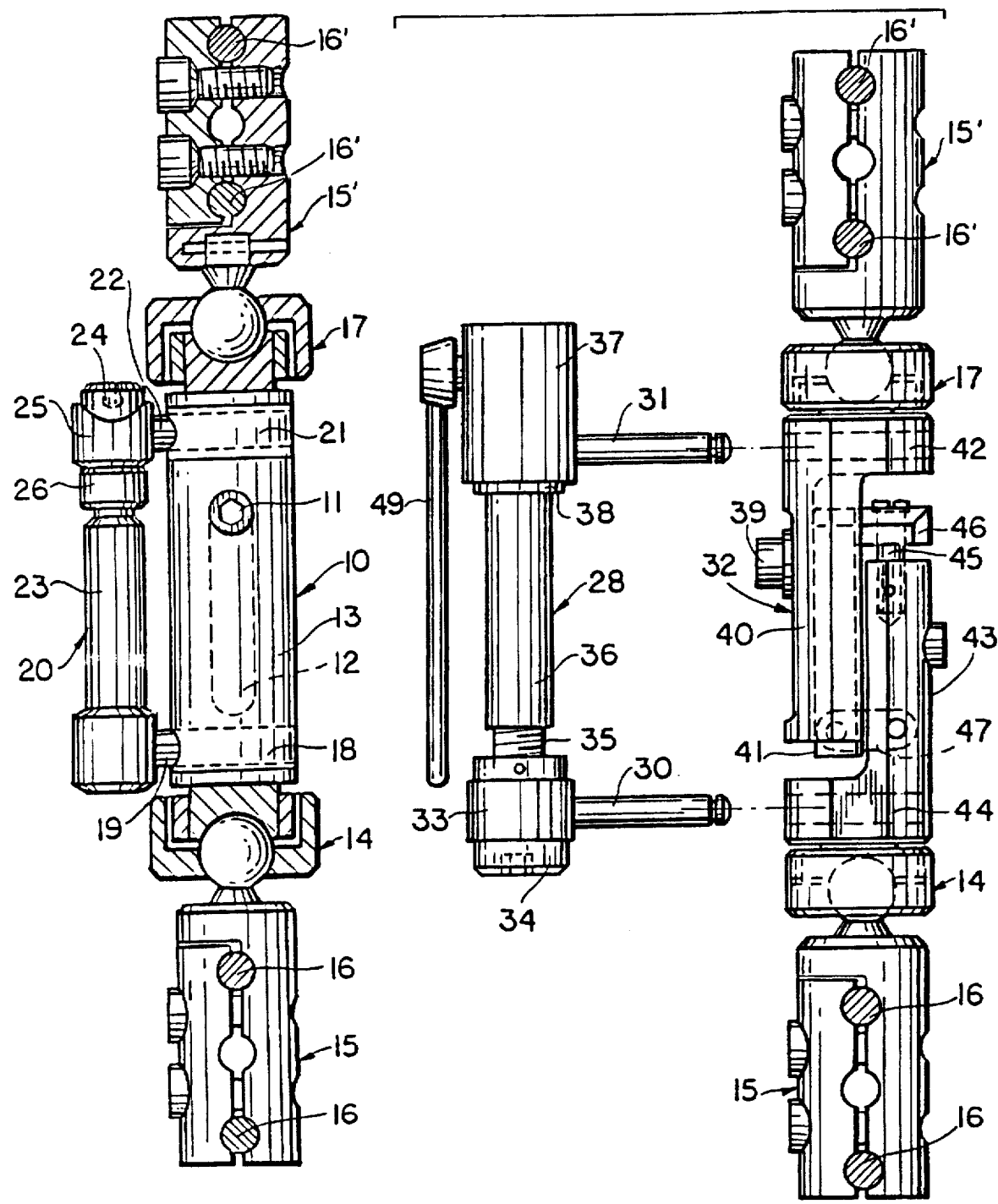
FIG. 1, labelled "PRIOR ART", is a view in side elevation and partly in longitudinal section, showing an external axial fixator with an accessory jacking device for precise setting and adjustment of the effective length of the fixator.
FIG. 2 is a similar view of a dynamic external axial fixator in exploded relation with a patient-operated accessory device of the invention, for transient distraction of the fixator.

The prior art device of FIG. 1 is generally as shown and described in said U.S. reissue patent, wherein an external axial fixator is seen to comprise an elongate central body 10 of telescopically related inner and outer body parts which can be adjusted as to overall effective length via a clamp bolt 11 which can secure these body parts to each other, for a given selected position of bolt 11 in an elongate slot 12 in the inner body part. One end of one of the body parts, e.g., the outer body part 13, has a ball-joint connection 14 to clamp means 15 for securely clamped anchoring reference to one or more bone-screws or pins 16 that will be understood to have been driven into bone at offset in one direction away from a fracture in the bone; the opposite end of the other body part, e.g., the inner body part, has a similar ball-joint connection 17 to similar clamp means 15' for securely clamped anchoring reference to bone screws or pins 16' that have been driven into the bone at opposite offset from the fracture site. Both ball joints are selectively lockable, to retain a given angular relationship of the axis of body 10 to the respective axes of clamps 15, 15', as appropriate for particular applications.

At its head or ball-joint connection end 18, the outer body part 13 has a transverse bore that is adapted to receive and locate a first pin 19 of a length-adjusting accessory 20; and similarly, at the opposite head or ball-joint connection end 21, the inner body part has a transverse bore that is adapted to receive and locate a second pin 22 of the accessory 20.

The length-adjusting accessory 20 comprises an internally threaded outer tubular member 23 which mounts pin 19 at its projecting end, and an inner threaded rod has a wrenchable head 24 at the opposite end. The inner threaded rod is wrench-actuated at 24 for adjustment of the extent of thread engagement within tubular member 21, and the head (24) end of the threaded rod seats on and is rotatable within a counterbore of a boss 25 which mounts pin 22. A lock nut 26, also engaged to the threaded rod, is run against boss 25 for locked retention of a given overall accessory length, i.e., a given separation of the accessory-mounting of pins 19, 22.

FIG. 2 shows an accessory device 28 of the invention, featuring a manually operable distraction function, in addition to the length-adjustment function described for the prior art accessory device of FIG. 1. Specifically, insertion pins 30, 31 mount the accessory to the body 32 of an external fixator which is preferably of the axially dynamic variety, suitably as shown and described in said U.S. Pat. No. 5,320,622. As shown, the lower pin 30 is mounted to a boss 33 which is axially located at the head end 34 of an elongate rod or first body part 35 that is in threaded engagement with the bore of an elongate tubular body part 36; and the upper pin 31 is mounted to a sleeve 37 that is axially slidable away from a fixed flange 38 on body part 36, for accommodation of a manually actuated transient distracting displacement of pin 31 with respect to pin 30. The mechanism for patient-operation to achieve such distraction is contained within sleeve 37 and is manually driven by a partial rotary cranking actuation of a handle 49, as will be described in greater detail in connection with FIG. 3.

Description of a dynamic axial fixator generally as shown in FIG. 2 is obtainable from said U.S. Pat. No. 5,320,622, which is hereby incorporated by reference. For present purposes, it suffices to note that overall length of body 32 is established by a bolt 39 which releasably secures a first elongate body member 40 to an elongate intermediate body member 41 at a given relation of longitudinally guided overlap of members 40, 41. At its upper end, body member 40 has an enlarged head 42 which is transversely bored to provide for guided insertion of upper pin 31 of the accessory 28, and head 42 will be understood to be equipped with a ball-joint connection 17 to upper clamp structure 15' as described for the prior art in FIG. 1. A second elongate body member 43 has an enlarged head 44 which is transversely bored to provide for guided insertion of the lower accessory pin 30, and head 44 will be understood to be equipped with a ball-joint connection 14 to lower clamp structure 15, as described for the prior art of FIG. 1. A longitudinal guide rod 45 fixed to and projecting beyond the upper end of body member 43 has bidirectionally axial and resiliently snubbed engagement to the laterally offset upper end 46 of intermediate body member 41. Finally, a short link 47 is pinned on parallel pivot axes in second body member 43 and in intermediate body member 41, wherein the two pivot axes define a geometric plane which is substantially normal to the longitudinal axis of the fixator, namely, wherein the longitudinal axis is on the geometric alignment of ball centers at the respective ball-joint connections 14, 17. Greater detail of the bidirectional snubbing action and structure will be found in said U.S. Pat. No. 5,320,622.

Figure 3:
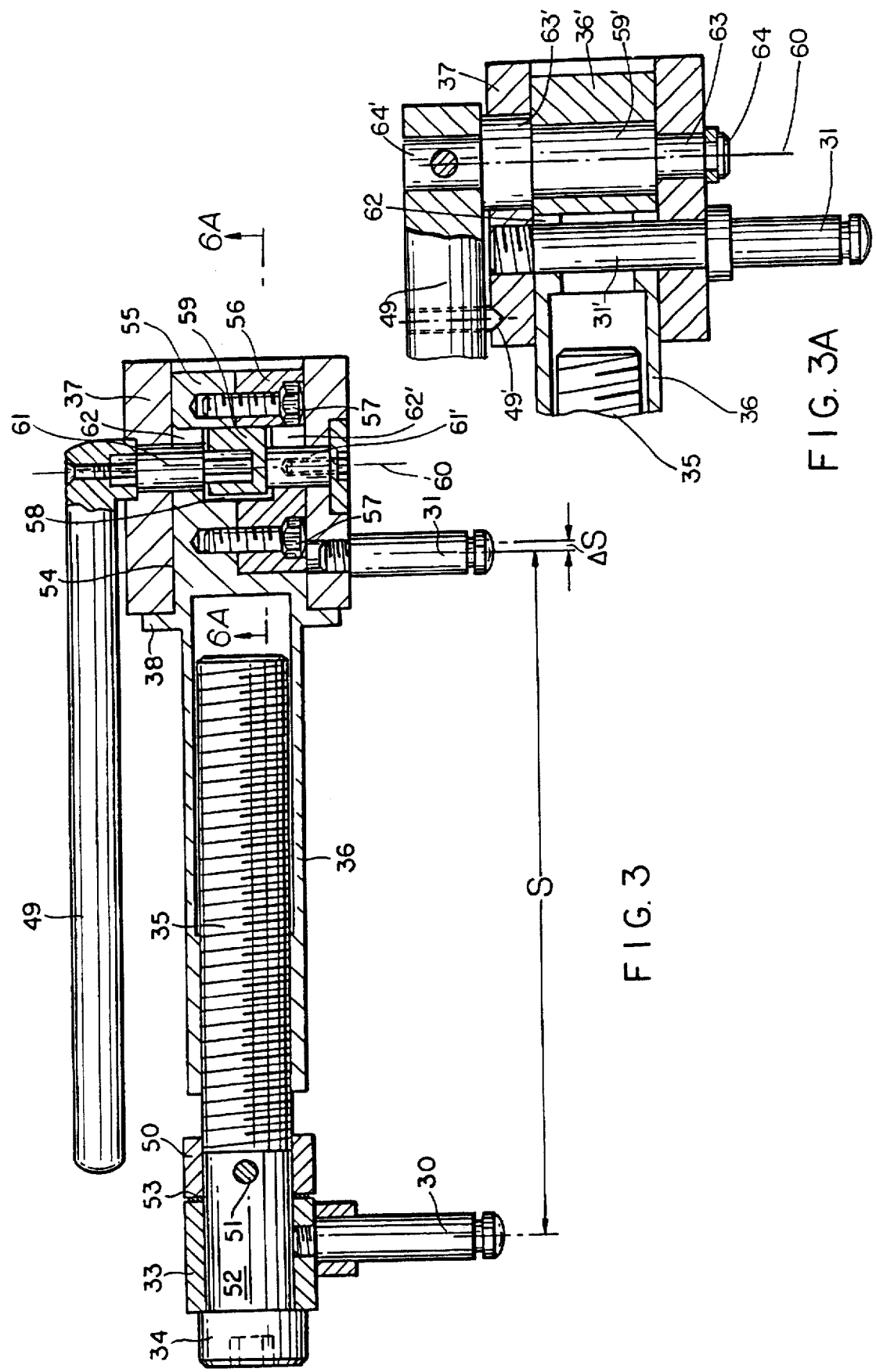
FIG. 3 is a view in longitudinal section of the accessory device of FIG. 2, to an enlarged scale.

In FIG. 3, parts which have already been identified will be recognized. In addition, the rotary but axially located relation of boss 33 to the inner body part 35 will be seen to be established by a collar 50 that is pinned at 51 to the unthreaded axially projecting shank end 52, adjacent head 34. A low-friction washer 53, as of nylon, between collar 50 and boss 33 assures smoothly wrenched rotation of body part 35, to establish an initial span S between the respective fixator-engageable means represented by pins 30, 31, for which condition sleeve 37 will be understood to be in its most leftward position, as in axially seated engagement with flange 38, with span S as determined by the nominal installed overall length of the fixator body 32, the same having been fixed by clamp bolt 39.

At its head end, the outer body part 36 is closed to establish an enlarged cylindrical land 54 for smooth axial guidance of sleeve 37, in its distraction displacement away from abutment with the shoulder or flange 38. As shown, this closed end comprises a first semicylindrical part 55 that is an integral formation of body part 36, and a second and separate semicylindrical part 56 that is bolted at 57 to secure parts 55, 56 to each other and thus complete the continuity of land 54. The confronting adjacent surfaces of the semicylindrical parts 55, 56 are similarly concave to establish a flat cavity wall 58 as a surface of cam-follower action, when handle 49 is operated to rotate a cam 59 in rising engagement with wall 58, thus incrementally and transiently imparting a distraction displacement ΔS to the pin 31 with respect to pin 30, i.e., to the fractured bone end secured at 15' with respect to the other bone end secured at 15. A rotary cam 59, which may be a cylindrical member or eccentric is mounted for gyrated rotation on a fixed transverse axis 60, involving diametrically opposed cylindrical bearing formations 61, 61' that are journalled in diametrically opposed bearing bores in sleeve 37. These bearing formations 61, 61' also pass through diametrically opposed short longitudinal slots 62, 62', by means of which cam 59 is rotatable within the head end of the tubular part 36, and it is also keyed against rotation and incrementally axially displaceable in slots 62, 62'. Various force-fitted engagements of separate parts in the succession 61, 62, 59, 62', 61' assure an effectively shaft-mounted eccentric at 59, with provision for positive cam actuation via partial cranked rotation of handle 49. Stated in other words, since rotary cam 59 may be cylindrical or eccentric and is mounted for gyrated rotation on a fixed transverse axis, the "throw" of the rotary cam can provide a total distracting displacement, for 180° or less of patient-operated transient handle (49) operation; this "180 degrees or less" can be expressed as "cam rotation being limited to partial rotation of less than 180 degrees", because cam rotation beyond 180 degrees will no longer provide the described distraction displacement, either for an eccentric or for gyrated rotation of a cylinder on or about a fixed axis.

FIG. 3A illustrates a construction alternative for the actuating end of the accessory 28 that has been described in connection with FIGS. 2 and 3. In FIG. 3A, the distal end of threaded body part 35 is seen within the bore of outer tubular body part 36. Sleeve 37 mounts the pin 31 by way of an extended shank 31' of pin, extending across the full diameter of the sleeve, with threaded distal-end engagement to the sleeve, as limited by a shoulder formation of pin 31. Within sleeve 37, the pin shank 31' freely passes through diametrically opposed openings in tubular body part 36; these openings may be oval, with longitudinal orientation of their major-axis dimension so as to develop a longitudinal clearance 62 for accommodating the axially distracting displaceability of sleeve 37 (and its mounting pin 31) with respect to body member 36. The cam 59' of FIG. 3A may be a cylindrical portion of a unitary part, which further comprises a distal-journal end 63 of smaller diameter, a proximal-journal end 63' of greater diameter, a distal grooved projection 64 for snap-ring retention, and a proximal-end projection 64' for pinned mounting of the handle 49; it is noted (1) that the elements 64, 63, 63', 64' of this unitary part are all on the axis of journal support by sleeve 37, with the axis of cam 59' eccentrically offset from axis 60, to the extent of desired distracting displaceability of pins 30, 31 with respect to each other, and that cam 59' is rotatable (with suitable clearance, not shown) in a transverse diametrically extending cam-following bore near the distal end of body member 36. In FIG. 3A, body member 36 is shown to have a solidly closed distal end 36' in which the cam-following bore is formed. A spring detent pin 49' carried by handle 49 is detent-engageable at a local detent recess in sleeve 37, to resiliently retain the longitudinally oriented zero-distraction position of handle 49 when not in use.

In the embodiment thus far discussed, in connection with FIGS. 2 and 3, the longitudinal span S to accord with points of connection to an installed fixator is adjustably set (at 34), with sleeve 37 seated against shoulder and with cam 59 at its low point in relation to the cam-follower wall 58. A partial rotation of the cam, manually imparted by handle 49, will engage cam 59 to wall 58 to effect a transient distraction displacement ΔS, as sleeve 37 develops a corresponding incremental axial offset from shoulder 38. Having thus distracted the dynamic fixator, the handle 49 can allow the fixator to return to its normal axially fixated relation of the involved bone connections, astride the fracture. It is currently recommended that the patient be taught and instructed to perform such transient distraction cycles in a relatively rapid succession of as many as ten cycles, repeated on prescribed periodic intervals each day. Illustratively, the effective cam rise may be 1 or as much as 2 mm, but preferably the distraction-effecting cam rise is in the range 0.8 to 1.2 mm.

Figure 6A:
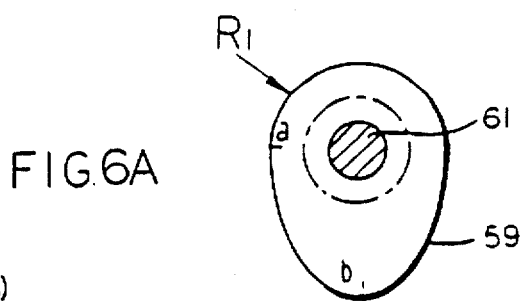
FIG. 6A is an enlarged and exaggerated axial-end view of a cam in the structure of FIG. 3, as viewed from the aspect 6A—6A of FIG. 3.
Figure 6B:
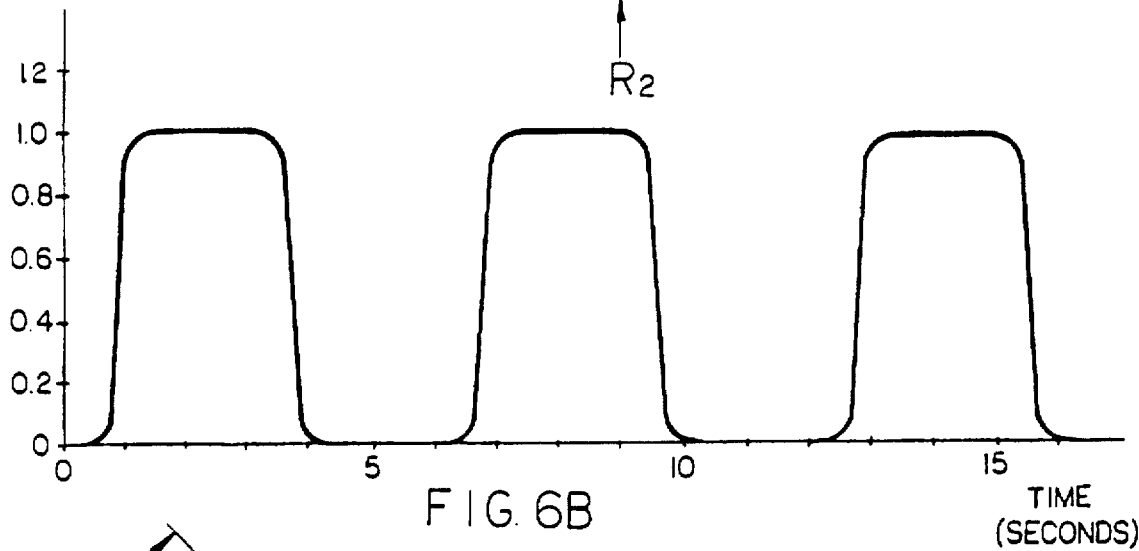
FIG. 6B is a graph to display a representative and presently preferred relation of distraction as a function of cyclically repeated time.

FIG. 6A is a simplified diagram to indicate present preference that, instead of cam 59 being cylindrical and eccentrically mounted with respect to the rotary axis 60, cam 59 has a somewhat ovate profile whereby to devote an extended proportion of its rise profile to achieving a substantially constant rate of rise, in the order of 4 mm/second between the acceleration rise and deceleration rise needed to complete a given fully distracting displacement stroke of pins 30, 31 with respect to each other. In FIG. 6A, this rise is a following of the change of cam (59) profile from a minimum radial extent $R_1$ to a maximum radial extent $R_2$, occurring as shown over a range of approximately 90 degrees of cam rotation between points a and b of the cam profile. And FIG. 6B is a graphical display of distraction displacement as a function of time, showing the presently preferred order of uniform rate (3 to 5 mm/sec) for substantially two-second dwells at each of the cam-following limits $R_1$, $R_2$, it being recommended that as many as ten recyclings of the indicated uniform-rate program be a typical protocol of patient-operated distraction.

It should also be noted that the described accessory of FIG. 3 lends itself to a more elaborate protocol of use, particularly once the patient has entered the weight-bearing phase of using his dynamic fixator. In this phase, the surgeon may prescribe incremental compressive action at the fracture site by reason of limited axial displaceability to transiently reduce the span S with each weight-bearing step via the fractured but dynamically fixated bone. To permit such transient compression, the inner body part 34 is incrementally wrenched so as to reduce the span S in incremental prescribed relief of the sleeve/shoulder engagement; if handle 49 and cam 59 are in the low-point position as shown in FIG. 3, then any axial clearance of the cam 59 with respect to the cam-follower wall 58 will be opened while the corresponding axial clearance is opened between sleeve 37 and shoulder 38. This shoulder clearance is available for the indicated transient incremental compressive action on the fracture site, with each weight-bearing step. And it will also be observed that, even though transient compressive action is available, the manually operated distraction cycle is also available, as long as the rise of cam 59 is sufficient to exceed the above-noted axial clearances.

Figure 4:
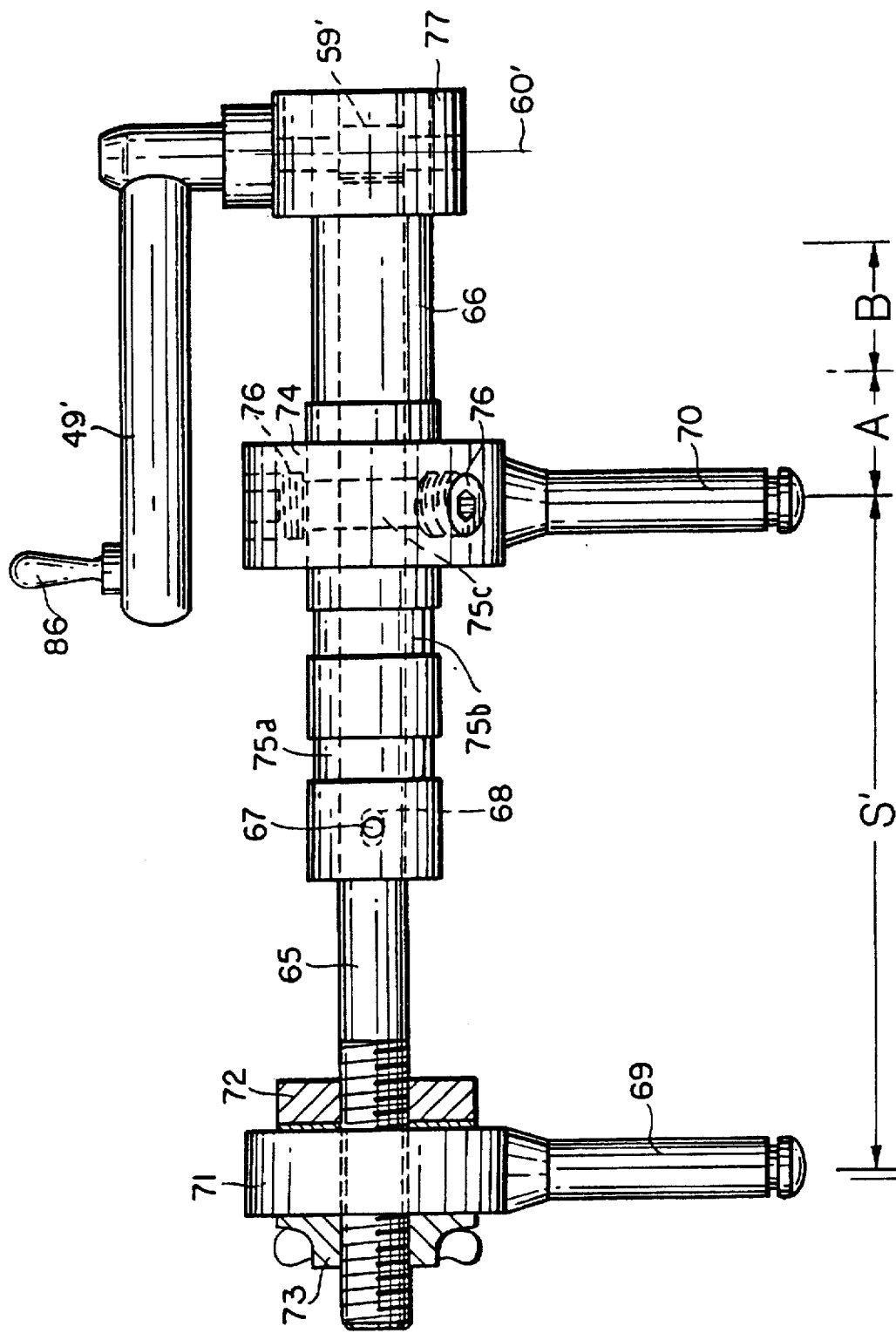
FIG. 4 is a view generally similar to FIG. 3 for another embodiment, as an alternative for the accessory device of FIG. 2.

In the embodiment of FIG. 3, transient distraction and/or compression of the fracture site involves transient axial displacement of sleeve 37 with respect to shoulder 38. The embodiment of FIG. 4 provides analogous operation by reason of transient axial displacement of an inner body part 65 with respect to an outer body part 66. The parts 65, 66 have limited telescopically guided fit, the limitation being axial by reason of a transverse pin 67 between diametrically spaced bores of the outer (tubular) body part 66, wherein pin 67 passes through a limited axial slot 68 of the inner body part 65. One (69) of the fixator-engageable pins 69, 70 of FIG. 4 is adjustably fixed to the inner body part 65, and the other (70) is adjustably fixed to the outer body part 66. To this end, the mounting hub 71 on pin 69 is shown to be carried at the exposed outer threaded end of body part 65, with nuts 72, 73 for fine setting of a given clamped axial position of pin 69; and the mounting hub 74 of the other pin 70 is shown to be selectively clamped at any given one of plural equally spaced locating grooves 75 (a,b,c) in the outer surface of body part 66, clamping being via three equally spaced set screws 76, only two of which appear in FIG. 4. A handle 49' and rotary cam 59', eccentrically offset from a transverse axis 60' of rotation in a fixed head 77 of body part 66, perform analogously to the action described for FIG. 3, except that in FIG. 4, manually cranked rotation of cam 59' through its rise will result cam driven incremental distracting displacement of the adjacent cam-following rod end of inner body part 65, to the extent shown at ΔS' in FIG. 4. For set-up purposes, it will be noted that the fixed spacing of intervals between grooves 75a, 75b, 75c enables rough increments to accommodate a given fixator requirement for the pin-to-pin span S', and that the threaded extent of the exposed end of inner body part 65 need be only slightly in excess of the span between two adjacent outer body grooves. Operation and fixator adaptation of the accessory of FIG. 4 are essentially as described for FIG. 3, except that optional basic span settings are greater for the case of FIG. 4, for example to the span (S'+A) or to the span (S'+A+B), beyond the span S' shown, all in accordance with whether hub 74 is set at groove 75b or at groove 75a.

Figure 5:
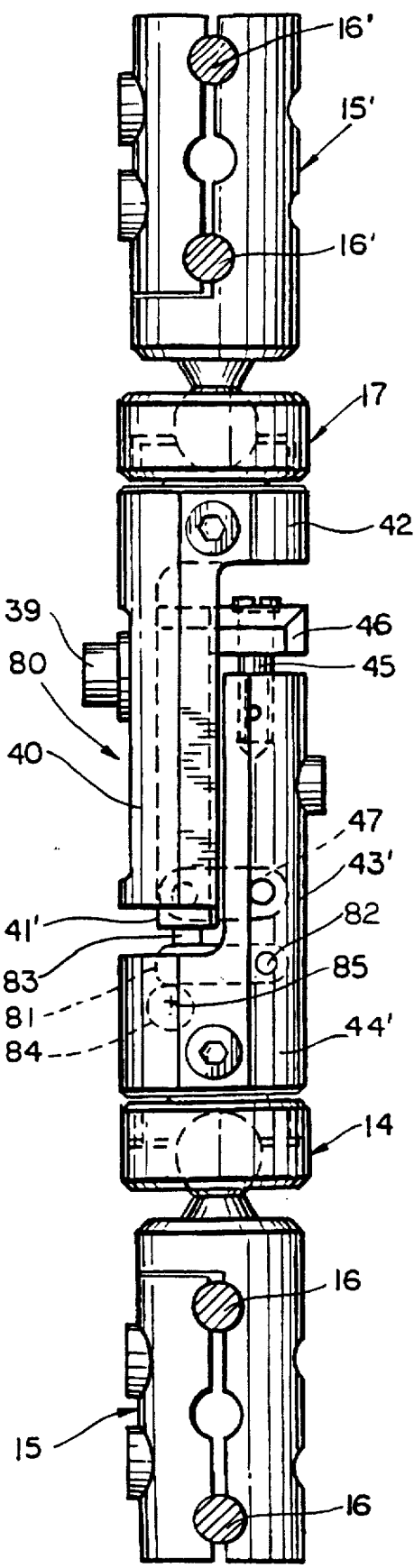
FIG. 5 is a simplified view in side elevation of a dynamic axial fixator in which the transient distraction function of FIGS. 3, 3A or 4 is a built-in feature of the fixator per se.

In FIG. 5, the manually operated function of transient distraction is a built-in feature of a dynamic axial fixator 80 of the general nature shown for the fixator in FIG. 2, but without requiring an accessory (28) to perform the transient distraction. In FIG. 5, the head end 44' of the outer body part 43' is slightly more axially elongate than is shown for head 44 of FIG. 2. And an idler arm 81 will be understood to be pivoted at 82 to body part 43' on an alignment parallel to and axially offset from the lower pivot for link 47. Idler arm 81 will also be understood to be accommodated within a recess in head 44'. For the unstressed condition shown for fixator 80 in FIG. 5, link 47 is oriented transverse to the longitudinal axis of the fixator body, and a projection 83 on the adjacent confronting end of intermediate body part 41' is poised for engagement by arm 81, with arm 81 substantially parallel to link 47. For transient distraction, a rotary cam or eccentric 84 is shown mounted for rotation on a transverse axis, schematically indicated at 85, in head 44'. It will be understood that the cam or eccentric 84 can be shaft-driven on axis 85, by a manual crank, not shown in FIG. 5 but as shown in FIG. 3 or FIG. 4. Eccentric throw incrementally distracts bone-screw clamp 15' with respect to bone-screw clamp 15.

Figure 7:
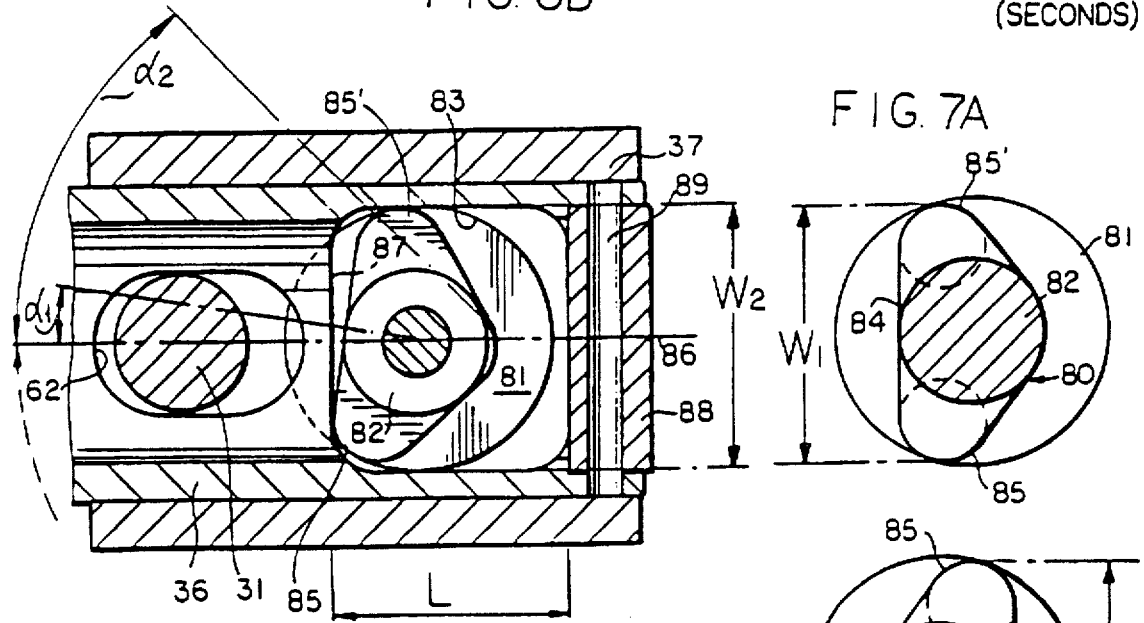
FIG. 7 is an enlarged fragmentary longitudinal section to illustrate a modified cam and cam-follower construction; the section plane includes the central longitudinal axis of the accessory device and is normal to the transverse axis of cam rotation.

In the modification of FIG. 7, the annular body member or sleeve 37 again overlaps and is guided for limited axial displacement on the tubular body member 36; and the fixator-engageable rod 31 derives fixed mounting from sleeve 37, at diametrically opposed locations. Rod 31 passes through tubular body member 36 via diametrically opposed slots 62, of sufficient axial extent to provide anti-rotational guidance of body member 36 with respect to sleeve 37 for all cam-driven axial displacements.

Figure 7A:
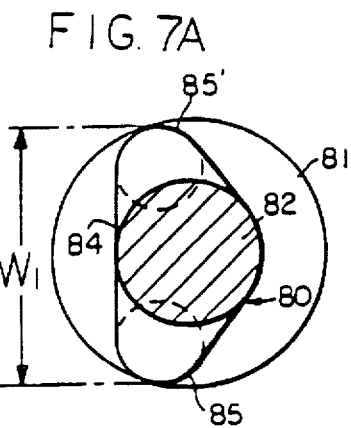
FIG. 7A is a view similar to FIG. 6A, for the modification of FIG. 7 and 7B is a 180 degree-reversed view.
Figure 7B:
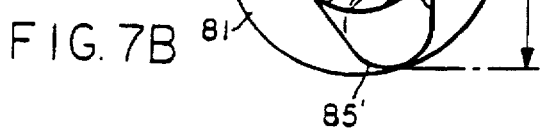

An important feature of FIG. 7 is the characterizing of cam and cam-follower action, which is further illustrated in connection with FIG. 7A. FIG. 7A displays only the cam 80, which is integral with or otherwise fixedly related to a proximal land 81 of greatest diameter and to a distal land 82 of lesser diameter; the land 81 will be understood to derive journal support in a diametrically oriented bore 83 (FIG. 7) through one side of sleeve 37, and land 82 will be understood to derive further journal support in a counterbore (not shown) through the opposite side of sleeve 37, with the operative profile of cam 80 interposed between lands 81, 82.

Cam 80 is characterized by a flat surface 84 which is normal to a central plane of symmetry through the axis of cam rotation, determined by the aligned centers of lands 81, 82. Outer rounded lobes 85, 85' symmetrically terminate the respective ends of surface 84 and determine an overall cam width $W_1$, approximately 75 percent of which is attributable to surface 84. The contour of cam 80 is completed by sloping back sides which are respectively tangent to the profiles of lobes 85, 85' and of land 82.

The described features of cam 80 will be recognized in FIG. 7, in the context of coacting cam-follower structure of the tubular member 36, wherein the drawing illustrates the relation of parts for an instant during the course of a distracting actuation of cam 80, namely, with cam 80 rotated a small fraction $\alpha_1$ of its full range $\alpha_2$ of displaceability from a zero-distraction condition wherein the flat surface 84 is normal to the central axis 86 of the tubular body member 36. Cam-follower structure is provided by diametrically opposite matching edges 87 of diametrically opposite generally rectangular openings, of body axial length L and transverse width $W_2$; the edges 87 may be said to lie in a geometrical plane that is normal to the central axis 86. Since body member 36 is tubular, the back wall of these rectangular openings is closed and defined by a plate 88, seated against a shoulder and fixed in position by a transverse pin 89. The transverse width dimension $W_2$ slightly exceeds the width $W_1$ of cam 80, but the length dimension L preferably is less than the width $W_1$ of cam 80.

In the course of continuing cam-80 rotation in the clockwise direction, the lower lobe 85 rides on both of the edges 87 of the opposed rectangular openings of tubular member 36, thus drawing sleeve 37 and its rod 31 in further distraction of the space S between the two rods 30, 31. And since the length L is preferably less than the cam width $W_1$, there comes a point at which cam lobe 85' strikes the back-closure plate 88. For the form shown, this limiting point determines the maximum angle $\alpha_2$ of hand-crank (49) operation of cam 80, namely approximately 45 degrees away from the zero-distraction position, at which point α is zero and hand crank 49 is parallel to the body axis of tubular member 36.

Thus far, all distraction displacements have been referred to as transient, meaning a hand-cranking of the full rise of the rotary cam or a part of said rise, as may be prescribed by the surgeon, the same being followed by return to the position of zero distraction. But it has also been indicated that a plurality of sequential distractions may be prescribed for a given event in a patient's therapy, in which case a crank extension on the handle, as at 86 in FIG. 4, may facilitate the patient's easy development of the sequence of distractions, through continuous manually driven rotation via crank extension 86.

While the invention has been described in the foregoing with particular reference to specific embodiments, it is to be appreciated that the invention is not limited to the embodiments described, but is encompassed by the broad wording of the appended claims which envisage modifications and variations to the described embodiments which would occur to those possessed of the relevant skills and knowledge. In particular, while the invention has been described in the foregoing with particular reference to orthopedic distraction devices, it would be a simple matter to modify the described devices to be capable of providing compressive displacement, either instead of or, selectively, in addition to distractive displacement. For example, the cam structure shown in FIG. 6A could be inverted about a horizontal plane bisecting the rotary axis 61 so as to provide compression rather than distraction, and other modifications which will readily occur to those possessed of the relevant skills could be made for enabling selective distraction and/or compression. Also, for example, if in FIG. 7 the described journal support of cam 80 in sleeve 37 were 180-degrees reversed, with the cam surface 84 flat against back plate 88 for a location of zero compression, any rotation of cam 80 would entail compressive displacement of the rods 30, 31 by reason of cam lobe coaction with plate 86.

Still further, recent clinical studies have indicated a desirable aspect of patient-actuated distraction whereby a lost motion designed into the actuator enables the patient to crank the actuating handle approximately 45° away from its normally stowed position of parallel orientation with respect to the elongation axis of the fixator body, before any cammed or other distracting displacement becomes operative. The embodiment of FIGS. 8 and 9 is illustrative of such a device, which will be understood to be built into the head end of a tubular outer body member 136; member 136 has adjustably threaded engagement to the elongate stem of an inner body member 135 which carries one of the fixator-engageable pins (not shown in FIGS. 8 or 9, but analogous to the showing at 30 in FIG. 3). At the head end of body member 136, an outer sleeve 137 mounts the other fixator-engageable pin 131 at diametrically opposite locations, with pin 131 passing through axially short slotted openings 162 which establish sufficient longitudinal clearance to accommodate axially distracting displaceability of sleeve 137. Within a counterbore at the head end of body member 136, a cam-follower element 155 in the form of a cylindrical plug is secured by pin means 156 to body member 136, and plug 155 features a transverse bore of generally square section; axially spaced walls 170, 171 of this generally square section provide cam-follower surfaces, for hand-actuated rotary displacement of a single-piece cam component 172, shown in the form of a crank shaft, in greater detail in FIGS. 10A and 10B.

The cam component 172 is seen to comprise spaced cylindrical bearings 173, 174 which will be understood to derive journal support in diametrically opposite large and small bores in sleeve 137. A crank pin element 175 integrally connects the spaced bearings 173, 174; and a stud formation 177 outward of bearing 173 provides a rugged means of handcrank 149 connection, the same being shown pinned at 178, to retain the connection. The stud formation 176 is suitably of square section, engaging a bore of similar square section in handle 149, and a locking pin 177 secures the square stud-to-bore engagement, with Allen-head driven thread engagement in the handle. A detent 149' carried by handle 149 provides releasable engagement to a central detent notch in the adjacent end of pin 131, to releasably hold the retracted position of handle 149, parallel to the longitudinal axis of body member 136.

The generally square section of the transverse bore of cam-follower plug 155 is sized to meet two criteria: first, angular throw of crank pin 175 extends free of cam-actuating engagement with either of the axially spaced cam-follower walls 170, 171 of the square-section, over a range of approximately ±45 degrees of rotary lost motion, and second, the entire crankshaft element 172 is configured at its reduced lower-bearing end 174 to permit simple threading assembly of crank pin 175 and bearing 174 regions via the sleeve bore in which the larger bearing 173 is journalled, and via the transverse square section bore in plug 155. This assembly is retained by snap-ring engagement to a peripheral groove 178 in the small-bearing end of crankshaft element 172.

The above-noted recent clinical studies have indicated a further-desirable aspect of patient-actuated distraction, whereby the described patient-operated distraction phase is limited to a period of say four or five weeks as from the end of the first week (of initially rigid bone fixation) to the end of the fifth week, the same to be followed throughout a remaining period of fixation wherein the described device of FIGS. 8 and 9 is resettable to a fixed compression of the fracture site; in this period of fixed compression, the same cam structure is relied upon to achieve a fixed compression displacement of the same magnitude as the patient-operated distraction displacement, but of course in the opposite direction. To assure that the patient can only operate the device for transient distraction as prescribed, provision is made in the form of a limit stop for preventing handle (149) operation in the wrong direction; provision is also made to assure that handle (149) cannot be patient-operated during his fixed-compression phase of fracture repair.

FIG. 13 is a simplified sectional view at a part of handle 149 to show a hinged circumferential clamp 180 secured by a clamp bolt 181 so as to position a stop projection 183 alongside the finger-engageable end of handle 149, thus limiting rotary actuation of handle to a single side of the at-rest position of parallel relation to the axis of body 136, namely, limitation to the side on which manually actuated distraction is possible, to the fully distracted relation depicted in FIG. 11.

On the other hand, when the physician determines that the period of patient-operated distraction has been completed and that fixed compression should be applied, the physician has two simple changes to make in the device of FIGS. 8 and 9. First, of course, he should remove the clamp 180 of FIG. 13, but before applying a similar clamp 184 to body 136 (FIG. 14), the locking pin 177 should be removed to permit handle 149 to assume a 90°-displaced engagement to the square stud formation 176 of cam 172. In this condition, handle 149 will extend normal to the axis of body 136 when the internal parts have the neutral relation depicted in FIG. 9. Having made this new square-stud to square-bore engagement, the locking pin 177 can be reset through a second bore 177' (see FIG. 10A) in stud 176, to lock the engagement, and the handle then actuated the 90-degrees of rotation necessary for realignment parallel with the axis of body 136. In the course of making this 90 degree displacement, and following an initial lost-motion handle displacement of about 45 degrees, the crankpin 175 of cam 172 will engage cam-follower surface 171, to accomplish the compression displacement, thus placing internal parts in the relation depicted in FIG. 11. Once the full-compression position (of handle 149) has been achieved, clamp 184 is set to body 136 (see FIG. 14), with its two projecting stops 185, 186 fixed to opposite sides of the finger-engageable end of the handle.

In a recommended use of the device of FIGS. 8 and 9, as in conjunction with a fixator of the variety of FIG. 1 or of FIG. 2, a recommended program of use is for the first week to be one of axial fixation, i.e., no compression and no distraction. Then for the next 4 to 5 weeks, the patient should be instructed to use the distraction feature as a rapid sequence of distraction-displacement cycles, e.g., a sequence of ten cycles each day, wherein the operative throw of cam 172 is in the range 1 to 2 mm (+ΔS). Upon the physician satisfying himself that the progress of fracture healing has sufficiently advanced, the described resetting to a fixed compression (–ΔS) is made for the remaining use of the fixation, with an option, in the case of the dynamic fixator of FIG. 2, to permit a period of dynamic compression via the fixator itself while the patient is in the weight-bearing phase of recovery.

What has been said for the device of FIGS. 8 and 9 will be understood to be equally applicable for the case of a fixator attachment, (as described for use with the fixator of FIG. 2), as well as for the case of embodiment in the construction of an external fixator per se. And in the case of a lost-motion displacement prior to cam/cam-follower engagement, there is a psychological advantage in providing the indicated approximately 45 degrees of lost motion because this enables the patient to get a better grip on the handle for the relatively rapid succession of cranking cycles he must make in the next 45-degree range, to achieve the described cyclical recurrence of distraction (+ΔS).

What is claimed is:

1. A patient-operated distraction device for selective periodic distraction of a fractured bone that has been set for retention by an external fixator having an elongate distensible fixator body connected to bone-screw or bone-pin clamps at the respective ends of said fixator body, said device comprising:
   (a) an elongate distractor body with first fixator-engageable means connected to one end of said distractor body and second fixator-engageable means connected to the opposite end of said distractor body, and
   (b) means including a manually operable rotary cam in one of said connections and on an axis transverse to the elongation of said distractor body for imparting a partial-turn cam-driven incremental distracting displacement of said first and second fixator-engageable means with respect to each other in response to at least a partial rotation of said rotary cam, said rotation of said cam being limited to partial rotation of less than 180 degrees.

2. The device of claim 1, in which said distractor body includes adjustable means at the other of said connections for selective adjustment of longitudinal space between said first and second fixator-engageable means, said adjustable means being operable independently of any rotation of said cam.

3. The device of claim 1, in which said cam is an eccentric.

4. The device of claim 1, in which said distractor body comprises inner and outer elongate body parts that are axially adjustably positionable over a range of coaxially engaged overlap of said body parts.

5. The device of claim 4, in which said one connection comprises a sleeve slidable on one of said body parts and mounting one of said fixator-engageable means, said rotary cam being on shaft means journalled in diametrically opposed bearing bores in said sleeve and engaged in diametrically opposed axially extending keying slots in said one body part.

6. The device of claim 5, in which said inner and outer body parts have threaded engagement to achieve the coaxially engaged relationship, there being an axially retained freely rotatable relation between said inner body part and the fixator-engageable means connected thereto.

7. The device of claim 1, in which said distractor body comprises inner and outer elongate body parts that are in coaxial relation and guided for relative axial displaceability over a range which is at least as great as the effective rise of said rotary cam, said cam being supported by said outer body part for rotation on a diametrically oriented axis transverse to the elongation of said outer body part and poised for cam-driven distracting displacement of said inner body part upon cam rotation via the rise of the cam.

8. The device of claim 7, in which said cam has a flat surface normal to a plane of symmetry which includes the rotary axis of the cam and which is between lobes which terminate the flat surface, and cam-follower means forming part of said inner body part and contained in a geometric plane normal to the axis of said inner body part.

9. The device of claim 8, in which said inner body means includes a stop formation engageable by one of said lobes to limit angular displaceability of said cam to less than 90 degrees either side of the condition of cam-flat engagement with said cam-follower means.

10. The device of claim 9, in which said angle is approximately 45 degrees.

11. The device of claim 7, in which one of said fixator-engageable means is adjustably securable at selectable locations along the length of the outer body part.

12. The device of claim 11, in which the other of said fixator-engageable means is adjustably securable to said inner body part via external threads along a portion of said inner body part.

13. A patient-operated distraction device for selective periodic distraction of a fractured bone that has been set for retention by an external fixator having an elongate distensible body connected to bone-screw or bone-pin clamps at respective ends of said body, said device comprising:
   (a) an elongate outer tubular body part and an elongate inner body part having one end in guided lap within said outer body part, said inner body part having its opposite end projecting out of and extending beyond one end of the guided lap within said inner body part;
   (b) first fixator-engageable means mounted to the outwardly projecting end of said inner body part, and second fixator-engageable means carried by said outer body part; and
   (c) means including a manually operable rotary cam journalled for rotation on a diametrically extending axis through said outer tubular body part and poised for cam action on said one end of said inner body part to axially displace said inner body part in the direction to incrementally spread apart said first and second fixator-engageable means with respect to each other as a function of manually actuated cam rotation, rotation of said cam being limited to partial rotation of less than 180 degrees.

14. The device of claim 13, in which selectively operable clamp means coacts between the outwardly projecting end of said inner body part and said first fixator-engageable means to selectively fix an adjusted longitudinal position of said fixator-engageable means along said inner body part.

15. The device of claim 13, in which selectively operable clamp means coacts between said outer body part and said second fixator-engageable means to selectively fix an adjusted longitudinal position of said fixator-engageable means along said outer body part.

16. The device of claim 13, in which the outwardly projecting end of said inner body part is externally threaded, and in which threaded means engaged to said externally threaded end is operative to fix a selected longitudinal position of mounting said first fixator-engageable means to said inner body part.

17. A patient-operated distraction device for selective periodic distraction of a fractured bone that has been set for retention by an external fixator having an elongate distensible body connected to bone screw or bone-pin clamps at the respective ends of said body, said device comprising:
   (a) an elongate internally threaded tubular body part and an elongate externally threaded body part engaged to said tubular body part, with a longitudinal end of said tubular body part extending at one end of said device and with the opposite longitudinal end of said threaded body part extending at the other longitudinal end of said device;
   (b) first fixator-engageable means in axially retained engagement with and supporting said threaded body part at said opposite longitudinal end for selective rotation with respect to said first fixator-engageable means;

(c) second fixator-engageable means in axially displaceable anti-rotational relation with said tubular part at said one longitudinal end; and (d) manually operated rotary cam means longitudinally interconnecting said second fixator-engageable means and said tubular body part, rotation of said cam means being limited to permit manually operated reciprocation of said cam within a range of less than 180 degrees.

18. The device of claim 17, wherein said cam means is an eccentric.

19. The device of claim 18, wherein said eccentric has a throw that is a very small fraction of the selectively available range of longitudinal adjustment by reason of the threaded engagement of said body parts.

20. The device of claim 17, in which said cam means is characterized by a profile such that manual actuation can produce a maximum distraction displacement in the range up to 2 mm.

21. The device of claim 17, wherein each of said fixator-engageable means mounts a fixator-engageable rod that extends radially of the axis of body-part engagement.

22. The device of claim 17, wherein said second fixator-engageable means includes an annular body guided for axial displaceability on said tubular body part, said cam means comprising rod means journalled for rotation in diametrically opposite bores of said annular body, said rod means having antirotational keying engagement with diametrically opposed longitudinal slots in said tubular body part, a cam formation on said rod means between the respective diametrically opposed journal and slot engagements, and a cam-follower formation fixedly related to said tubular body part and poised with respect to the rise of said cam formation to incrementally and longitudinally spread apart said first and second fixator-engageable means upon rod rotation.

23. The device of claim 22, in which said cam means is a one-piece crankshaft wherein said cam formation is a crank-pin portion and said rod means is integrally formed with said crank-pin portion.

24. The device of claim 17, in which each of said fixator-engageable means mounts a fixator-engageable rod that extends radially of the axis of body-part engagement, said second fixator-engageable means including an annular body in axial overlap of a region of said tubular body part, the fixator-engageable rod of said second fixator-engageable means being mounted to said annular body at diametrically opposite locations and having antirotational guidance at passage through diametrically opposite slot formations of said tubular body part, said tubular body part having further diametrically opposite openings of generally rectangular configuration wherein diametrically opposite cam-follower edges are in a geometric plane that is normal to the axis of said tubular body part, said cam means being journalled in said annular body for rotation on a diametrically extending axis through said generally rectangular openings, and said cam means having a flat surface engaged to said cam-follower edges for a first condition of zero distraction, said flat surface terminating with lobe formations at like but opposite offsets from a central plane of symmetry that (a) is normal to said flat surface and (b) includes the journal axis of said cam means, whereby initial actuating displacement of said cam means away from said first condition is accompanied by a maximum rate of cam-driven axial distraction per unit angular displacement of said cam means.

25. The device of claim 17, wherein said tubular part includes a radial flange at axial offset from its interconnection with said second fixator-engageable means, said second fixator-engageable means including an annular body guided for axial displaceability on said axial offset, said cam means comprising rod means journalled for rotation in diametrically opposite bores of said annular body, said rod means having antirotational keying engagement with diametrically opposed longitudinal slots in said tubular body part, said rod means including a cam formation between the respective diametrically opposed journal and slot engagements, and a cam-follower formation fixedly related to said tubular body part and poised with respect to the rise of said cam formation to incrementally and longitudinally spread apart said first and second fixator-engageable means upon rod rotation.

26. The device of claim 17, in which said cam means is a crank-pin portion of a crankshaft carried by said second fixator-engageable means, said crank-pin portion having coaction with a cam-follower-wall portion of said tubular body part.

27. The device of claim 26, in which said crank-pin portion has a throw that is a very small fraction of the selectively available range of longitudinal adjustment by reason of the threaded engagement of said body parts.

28. A patient-operated distraction device for elective periodic distraction of a fractured bone that has been set for retention by an external fixator having an elongate distensible fixator body connected to bone-screw or bone-pin clamps at the respective ends of said fixator body, said device comprising:

(a) an elongate distractor body having first and second axially guided parts, with first fixator-engageable means connected to one of said parts at one end of said distractor body and second fixator-engageable means connected to the other of said parts at the opposite end of said distractor body; and (b) manually operable rotary-cam means carried by one of said parts and reacting with said other of said parts to develop a transient manually driven incremental relative axially distracting displacement of said parts and therefore of said bone-screw clamps with respect to each other, rotation of said cam means being limited to permit manual rotation of said cam means within a range of partial rotation which is at least no greater than 180 degrees.

29. The device of claim 28, in which said manually operable means is further operative to develop a manually driven incremental axially compressing displacement of said body parts and, therefore, of said bone-screw clamps with respect to each other.

30. The device of claim 29, including stop means engageable between said manually operable means and one of said parts and selectively operable for determining in a first setting a first condition of variable distraction-displacement actuation, and for determining in a second setting a second condition of fixed compression-displacement actuation.

31. The device of claim 28, in which operation of said manually operable means includes a lost-motion connection, whereby transient distraction displacement occurs after an initial take-up of said lost-motion connection.

32. A patient-operated distraction device for selective periodic distraction of a fractured bone that has been set for retention by an external fixator having an elongate distensible fixator body connected to bone-screw or bone-pin clamps at the respective ends of said fixator body, said device comprising:

(a) an elongate distractor body with first fixator-engageable means connected to one end of said distractor body and second fixator-engageable means connected to the opposite end of said distractor body, said body comprising inner and outer elongate body parts that are axially adjustably positionable over a range of coaxially engaged overlap of said body parts; and (b) means including a manually operable rotary cam in one of said connections and on an axis transverse to the elongation of said distractor body for imparting a cam-driven incremental distracting displacement of said first and second fixator-engageable means with respect to each other in response to at least a partial rotation of said rotary cam, said one connection comprising a sleeve slidable on one of said body parts and mounting one of said fixator-engageable means, said-rotary cam being on shaft means journalled in diametrically opposed bearing bores in said sleeve and engaged in diametrically opposed axially extending keying slots in said one body part.

33. The device of claim 32, in which said inner and outer body parts have threaded engagement to achieve the coaxially engaged relationship, there being an axially retained freely rotatable relation between said inner body part and the fixator-engageable means connected thereto.

* * * * *